United States Patent
Rizoiu et al.

(10) Patent No.: US 7,415,050 B2
(45) Date of Patent: Aug. 19, 2008

(54) ELECTROMAGNETIC ENERGY DISTRIBUTIONS FOR ELECTROMAGNETICALLY INDUCED MECHANICAL CUTTING

(75) Inventors: Ioana M. Rizoiu, San Clemente, CA (US); Andrew I. Kimmel, San Clemente, CA (US)

(73) Assignee: Biolase Technology, Inc., Irvine, CA (US)

( * ) Notice: Subject to any disclaimer, the term of this patent is extended or adjusted under 35 U.S.C. 154(b) by 0 days.

(21) Appl. No.: 11/606,660

(22) Filed: Nov. 29, 2006

(65) Prior Publication Data

US 2008/0069172 A1     Mar. 20, 2008

Related U.S. Application Data

(63) Continuation-in-part of application No. 11/523,492, filed on Sep. 18, 2006.

(51) Int. Cl.
*H01S 3/10* (2006.01)
*A61B 18/18* (2006.01)

(52) U.S. Cl. .......................................... 372/25; 606/10
(58) Field of Classification Search ............ 372/1, 372/25, 26, 30, 75; 606/10
See application file for complete search history.

(56) References Cited

U.S. PATENT DOCUMENTS

| | | | |
|---|---|---|---|
| 5,181,223 A | 1/1993 | Baer et al. | |
| 5,192,279 A | 3/1993 | Samuels et al. | |
| 5,199,870 A | 4/1993 | Steiner et al. | 372/69 |
| 5,200,966 A | 4/1993 | Esterowitz et al. | |
| 5,272,713 A * | 12/1993 | Sobey et al. | 372/69 |
| 5,363,387 A | 11/1994 | Sinofsky | |
| 5,401,171 A | 3/1995 | Paghdiwala | 372/69 |
| 5,415,652 A | 5/1995 | Mueller et al. | |
| 5,423,798 A | 6/1995 | Crow | 433/215 |
| 5,458,594 A | 10/1995 | Mueller et al. | |
| 5,554,029 A | 9/1996 | Kowalyk et al. | |
| 5,623,510 A | 4/1997 | Hamilton et al. | |
| 5,741,247 A | 4/1998 | Rizoiu et al. | |
| 5,785,521 A | 7/1998 | Rizoiu et al. | 372/75 |
| 5,846,080 A | 12/1998 | Schneider | |
| 5,940,425 A | 8/1999 | Lasser et al. | |
| 5,968,037 A | 10/1999 | Rizoiu et al. | 433/215 |
| 6,050,991 A | 4/2000 | Guillet | |
| 6,086,366 A | 7/2000 | Mueller et al. | 606/13 |

(Continued)

OTHER PUBLICATIONS

U.S. Appl. No. 09/848,010, filed May 2, 2001, Rizoiu et al.

(Continued)

*Primary Examiner*—Armando Rodriguez
(74) *Attorney, Agent, or Firm*—Stout, Uxa, Buyan & Mullins, LLP

(57) ABSTRACT

Output optical energy pulses including relatively high energy magnitudes at the beginning of each pulse are disclosed. As a result of the relatively high energy magnitudes which lead each pulse, the leading edge of each pulse includes a relatively large slope. This slope is preferably greater than or equal to 5. Additionally, the full-width half-max value of the output optical energy distributions are between 0.025 and 250 microseconds and, more preferably, are about 70 microseconds. A flashlamp is used to drive the laser system, and a current is used to drive the flashlamp. A flashlamp current generating circuit includes a solid core inductor which has an inductance of 50 microhenries and a capacitor which has a capacitance of 50 microfarads.

19 Claims, 8 Drawing Sheets

U.S. PATENT DOCUMENTS

| | | | |
|---|---|---|---|
| 6,086,367 | A | 7/2000 | Levy |
| 6,090,102 | A | 7/2000 | Telfair et al. |
| 6,099,520 | A | 8/2000 | Shimoji |
| 6,129,723 | A | 10/2000 | Anderson et al. |
| 6,179,830 | B1 | 1/2001 | Kokubu ............... 606/2 |
| 6,213,998 | B1 | 4/2001 | Shen et al. ............ 606/13 |
| 6,231,567 | B1 | 5/2001 | Rizoiu et al. |
| 6,235,017 | B1 | 5/2001 | Jegorov et al. |
| 6,288,499 | B1 | 9/2001 | Rizoiu et al. |
| 6,350,123 | B1 | 2/2002 | Rizoiu et al. |
| 6,389,193 | B1 | 5/2002 | Kimmel et al. ......... 315/200 A |
| 6,458,120 | B1 | 10/2002 | Shen et al. |
| 6,533,775 | B1 | 3/2003 | Rizoiu |
| 6,544,256 | B1 | 4/2003 | Rizoiu et al. |
| 6,561,803 | B1 | 5/2003 | Rizoiu et al. |
| 6,567,582 | B1 | 5/2003 | Rizoiu et al. |
| 6,607,524 | B1 | 8/2003 | LaBudde et al. |
| 6,610,053 | B1 | 8/2003 | Rizoiu et al. |
| 6,616,447 | B1 | 9/2003 | Rizoiu et al. |
| 6,616,451 | B1 | 9/2003 | Rizoiu et al. |
| 6,631,153 | B2 | 10/2003 | Sumiyoshi et al. |
| 6,669,685 | B1 | 12/2003 | Rizoiu et al. |
| 6,744,790 | B1 | 6/2004 | Tilleman et al. |
| 6,821,272 | B2 | 11/2004 | Rizoiu et al. |
| 6,829,427 | B1 | 12/2004 | Becker |
| 6,942,658 | B1 | 9/2005 | Rizoiu et al. |
| 7,068,912 | B1 | 6/2006 | Becker |
| 7,108,693 | B2 | 9/2006 | Rizoiu et al. |
| 7,288,086 | B1 * | 10/2007 | Andriasyan ............ 606/14 |

OTHER PUBLICATIONS

U.S. Appl. No. 10/178,080, filed Jun. 21, 2002, Andriasyan, Manvel A.

U.S. Appl. No. 10/858,557, filed Jun. 1, 2004.

Observation of enhanced thermal lensing due to near-Gaussian pump energy deposition in a laser-diode side-pumped Nd:YAG laser: David Welford, David M. Rines, Bradley J. Dinerman, and Robert Martinsen; Ieee Journal of Quantum Electronics, vol. 28, No. 4, 1992.

High power 1.9 micron pumped solid-state holmium lasers, Budni et al; Lasers and Electro-Optics, 2000. (CLEO 2000). Conference on May 7-12, 200, p. 54.

CW Laser Operation From Er:YAG, Er:GGG, Er:YSGG and Er:BYF, Dinerman, B. J. et al; Lasers and Electro-Optics Society Annual Meeting, 1992. LEOS '92, Conference Proceedings, Nov. 16-19, 1992, pp. 310-311.

* cited by examiner

ELECTROMAGNETIC ENERGY DISTRIBUTIONS FOR ELECTROMAGNETICALLY INDUCED MECHANICAL CUTTING

CROSS-REFERENCE TO RELATED APPLICATIONS

This application is a continuation-in-part of co-pending U.S. application Ser. No. 11/523,492, filed Sep. 18, 2006 and entitled ELECTROMAGNETIC ENERGY DISTRIBUTIONS FOR ELECTROMAGNETICALLY INDUCED MECHANICAL CUTTING which is commonly assigned and the contents of which are expressly incorporated herein by reference.

BACKGROUND OF THE INVENTION

1. Field of the Invention

The present invention relates generally to lasers and, more particularly, to devices for generating output optical energy distributions.

2. Description of Related Art

A variety of laser systems are present in the prior art. A solid-state laser system generally comprises a laser rod for emitting coherent light and a stimulation source for stimulating the laser rod to emit the coherent light. Flashlamps are typically used as stimulation sources for Erbium laser systems, for example. Diodes may be used instead of flashlamps for the excitation source. The use of diodes for generating light amplification by stimulated emission is discussed in the book Solid-State Laser Engineering, Fourth Extensively Revised and Updated Edition, by Walter Koechner, published in 1996, the contents of which are expressly incorporated herein by reference.

Prior art laser diode pumped lasers have been either end-pumped, as demonstrated in FIG. 1a or side-pumped. End pumping configurations can be more efficient and can produce a better transverse mode. In FIG. 1a, wherein "HR" denotes a high reflectivity element and "OC" denotes an output coupling element, laser output is focused into a fiber via a lens. Side pumping constructions, on the other hand, can be more scalable therefore enabling the generation of relatively high laser power and energy.

The excitation source (e.g., flashlamp) is driven by a current (e.g., a flashlamp current), which comprises a predetermined pulse shape and a predetermined frequency. The flashlamp current drives the flashlamp at the predetermined frequency, to thereby produce an output flashlamp light distribution having substantially the same frequency as the flashlamp current. This output flashlamp light distribution from the flashlamp drives the laser rod to produce coherent light at substantially the same predetermined frequency as the flashlamp current. The coherent light generated by the laser rod has an output optical energy distribution over time that generally corresponds to the pulse shape of the flashlamp current.

The pulse shape of the output optical energy distribution over time typically comprises a relatively gradually rising energy that ramps up to a maximum energy, and a subsequent decreasing energy over time. The pulse shape of a typical output optical energy distribution can provide a relatively efficient operation of the laser system, which corresponds to a relatively high ratio of average output optical energy to average power inputted into the laser system.

The prior art pulse shape and frequency may be suitable for thermal cutting procedures, for example, where the output optical energy is directed onto a target surface to induce cutting. New cutting procedures, however, do not altogether rely on laser-induced thermal cutting mechanisms. More particularly, a new cutting mechanism directs output optical energy from a laser system into a distribution of atomized fluid particles located in a volume of space just above the target surface. The output optical energy interacts with the atomized fluid particles causing the atomized fluid particles to expand and impart electromagnetically-induced mechanical cutting forces onto the target surface. As a result of the unique interactions of the output optical energy with the atomized fluid particles, typical prior art output optical energy distribution pulse shapes and frequencies have not been especially suited for providing optical electromagnetically-induced mechanical cutting. Specialized output optical energy distributions are required for optimal cutting when the output optical energy is directed into a distribution of atomized fluid particles for effectuating electromagnetically-induced mechanical cutting of the target surface.

SUMMARY OF THE INVENTION

The output optical energy distributions of the present invention comprise relatively high energy magnitudes at the beginning of each pulse. As a result of these relatively high energy magnitudes at the beginning of each pulse, the leading edge of each pulse comprises a relatively large slope. This slope is preferably greater than or equal to 5. Additionally, the full-width half-max (FWHM) values of the output optical energy distributions are greater than 0.025 microseconds. More preferably, the full-width half-max values are between 0.025 and 250 microseconds and, more preferably, are between 10 and 150 microseconds. The full-width half-max value is about 70 microseconds in the illustrated embodiment. A flashlamp is used to drive the laser system, and a current is used to drive the flashlamp. A flashlamp current generating circuit comprises a solid core inductor having an inductance of about 50 microhenries and a capacitor having a capacitance of about 50 microfarads.

In accordance with one aspect of the present invention, a method of cutting or ablating hard tissue is disclosed, comprising the steps of providing a gain medium, a diode array, and an optical cavity; placing the gain medium and the diode array within the optical cavity so that the diode array is optically aligned to side pump the gain medium; activating the diode array to light pump the gain medium and generate laser light; and directing the laser light onto the hard tissue to cut or ablate the hard tissue.

In accordance with another aspect of the present invention, a method of cutting or ablating hard tissue, comprises the steps of providing a gain medium, a diode light pump, and an optical cavity; placing the gain medium and the diode light pump within the optical cavity so that the diode light pump is optically aligned to light pump the gain medium; activating the diode light pump to light pump the gain medium and generate laser light; and directing the laser light onto the hard tissue to cut or ablate the hard tissue.

According to another aspect of the invention, an apparatus for cutting or ablating hard tissue, comprises an optical cavity; a gain medium disposed within the optical cavity; a diode light pump disposed within the optical cavity and optically aligned to light pump the gain medium to generate laser light, wherein the generated laser light has a wavelength and power density suitable for cutting and ablating hard tissue.

In any of the above aspects, the gain medium may comprise a laser rod, such as an Erbium-based laser rod. More particularly, the gain medium may comprise an Erbium-based crystalline laser rod for generating laser light in a range between 1.73 and 2.94 microns. The laser light can be generated in the TEMoo mode to overcome thermal effects. In accordance with a method of the present invention, the hard tissue can comprise, for example, tooth or bone tissue. Temporal pulse control can be used to attain a uniform temporal pulse pattern. In another embodiment, gain switching or Q-switching can be used to attain the uniform temporal pulse pattern. The diode light pump can comprise a diode array, and the diode array can be optically aligned to side pump the gain medium. The diode light pump can be placed within the optical cavity so that the diode array is optically aligned to side pump the gain medium.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112.

Any feature or combination of features described herein are included within the scope of the present invention provided that the features included in any such combination are not mutually inconsistent as will be apparent from the context, this specification, and the knowledge of one skilled in the art. In addition, any feature or combination of features may be specifically excluded from any embodiment of the present invention. For purposes of summarizing the present invention, certain aspects, advantages and novel features of the present invention are described. Of course, it is to be understood that not necessarily all such aspects, advantages or features will be embodied in any particular implementation of the present invention. Additional advantages and aspects of the present invention are apparent in the following detailed description and claims.

BRIEF DESCRIPTION OF THE DRAWINGS

FIG. 7 is a close-up view of a pulse of FIG. 6a.

DETAILED DESCRIPTION OF THE PRESENTLY PREFERRED EMBODIMENTS

Figure 1:
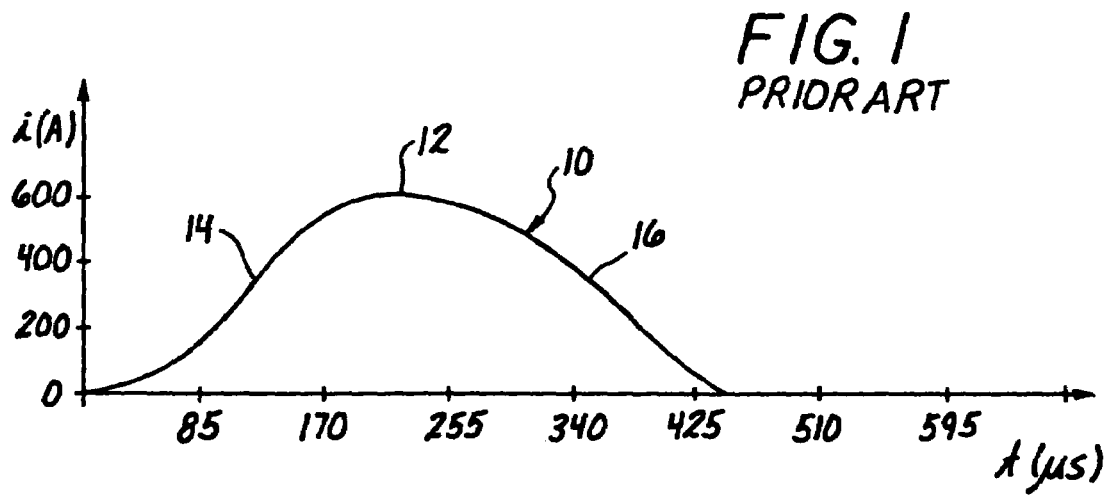
FIG. 1 is a plot of flashlamp-driving current versus time according to the prior art.

Reference will now be made in detail to particular embodiments of the invention, examples of which are illustrated in the accompanying drawings. Wherever possible, the same or similar reference numbers are used in the drawings and the description to refer to the same or like parts. It should be noted that the drawings are in simplified form and are not to precise scale. In reference to the disclosure herein, for purposes of convenience and clarity only, directional terms, such as, top, bottom, left, right, up, down, over, above, below, beneath, rear, and front, are used with respect to the accompanying drawings. Such directional terms should not be construed to limit the scope of the invention in any manner.

Although the disclosure herein refers to certain illustrated embodiments, it is to be understood that these embodiments are presented by way of example and not by way of limitation. The intent of the following detailed description, although discussing exemplary embodiments, is to be construed to cover all modifications, alternatives, and equivalents of the embodiments as may fall within the spirit and scope of the invention as defined by the appended claims.

Referring more particularly to the drawings, FIG. 1 illustrates a plot of flashlamp-driving current versus time according to the prior art. The flashlamp-driving current 10 initially ramps up to a maximum value 12. The initial ramp 14 typically comprises a slope (current divided by time) of between 1 and 4. After reaching the maximum value 12, the flashlamp-driving current 10 declines with time, as illustrated by the declining current portion 16. The prior art flashlamp-driving current 10 may typically comprise a frequency or repetition rate of 1 to 15 hertz (Hz). Additionally, the flashlamp-driving current 10 of the prior art may typically comprise a pulse width greater than 300 microseconds. The full-width half-max value of the flashlamp-driving current 10 is typically between 250 and 300 microseconds. The full-width half-max value is defined as a value of time corresponding to a length of the full-width half-max range plotted on the time axis. The full-width half-max range is defined on the time axis from a beginning time, where the amplitude first reaches one half of the peak amplitude of the entire pulse, to an ending time, where the amplitude reaches one half of the peak amplitude a final time within the pulse. The full-width half-max value is the difference between the beginning time and the ending time.

Figure 2:
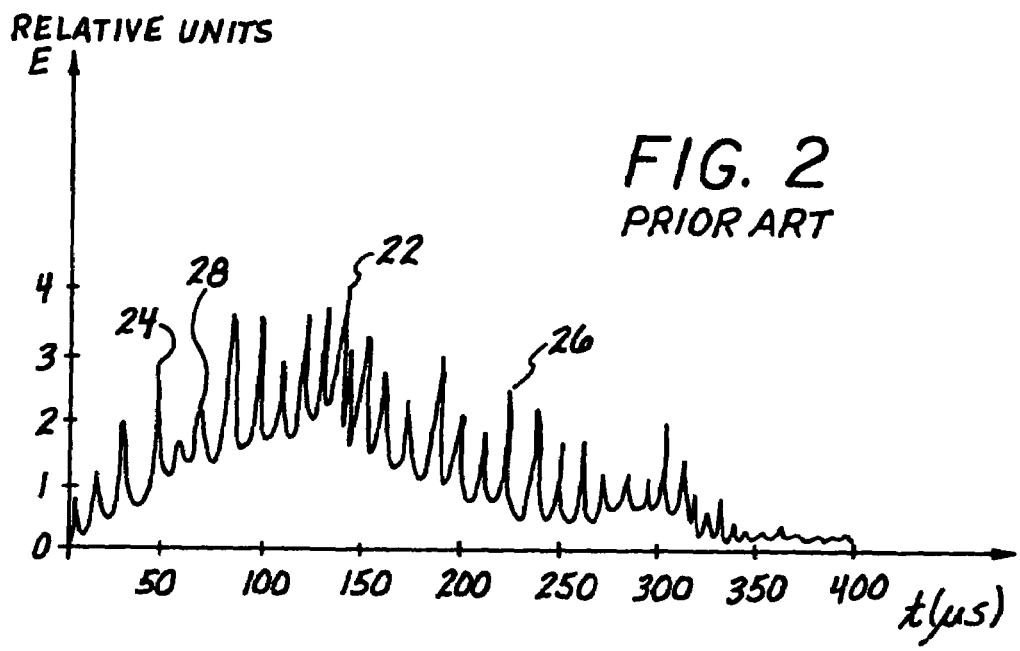
FIG. 2 is a plot of output optical energy versus time for a laser system according to the prior art.

FIG. 2 illustrates a plot of energy versus time for the output optical energy of a typical prior art laser. The output optical energy distribution 20 generally comprises a maximum value 22, an initial ramp 24, and a declining output energy portion 26. The micropulses 28 correspond to population inversions within the laser rod as coherent light is generated by stimulated emission. The average power of the laser can be defined as the power delivered over a predetermined period of time, which typically comprises a number of pulses. The efficiency of the laser system can be defined as a ratio of the output optical power of the laser, to the input power into the system that is required to drive the flashlamp. Typical prior art laser systems are designed with flashlamp-driving currents 10 and output optical energy distributions 20 which optimize the efficiency of the system.

Figure 3:
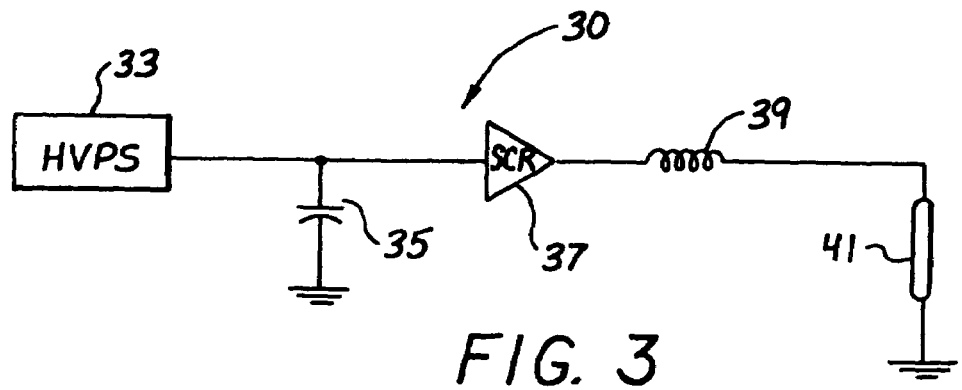
FIG. 3 is a schematic circuit diagram illustrating a circuit for generating a flashlamp-driving current in accordance with the present invention.

FIG. 3 illustrates a flashlamp-driving circuit 30 according to the presently preferred embodiment. The flashlamp-driving circuit 30 comprises a high-voltage power supply 33, a capacitor 35, a rectifier 37, an inductor 39, and a flashlamp 41. The capacitor 35 is connected between the high-voltage power supply 33 and ground, and the flashlamp 41 is connected between the inductor 39 and ground. The high-voltage power supply 33 preferably comprises a 1500 volt source, having a charging rate of 1500 Joules per second. The flashlamp 41 may comprise a 450 to 700 torr source and, preferably, comprises a 450 torr source. The capacitor 35 preferably comprises a 50 microfarad capacitor, and the rectifier 37 preferably comprises a silicon-controlled rectifier. The inductor 39 preferably comprises a 50 microhenry solid-core inductor. In alternative embodiments, the inductor 39 may comprise a 13 microhenry inductance. In still other alternative embodiments, the inductor 39 may comprise inductance values of between 10 and 15 micro-henries. Other values for the inductor 39 and the capacitance 35 may be implemented in order to obtain flashlamp-driving currents having relatively large leading amplitudes, for example, as discussed below.

Figure 6:
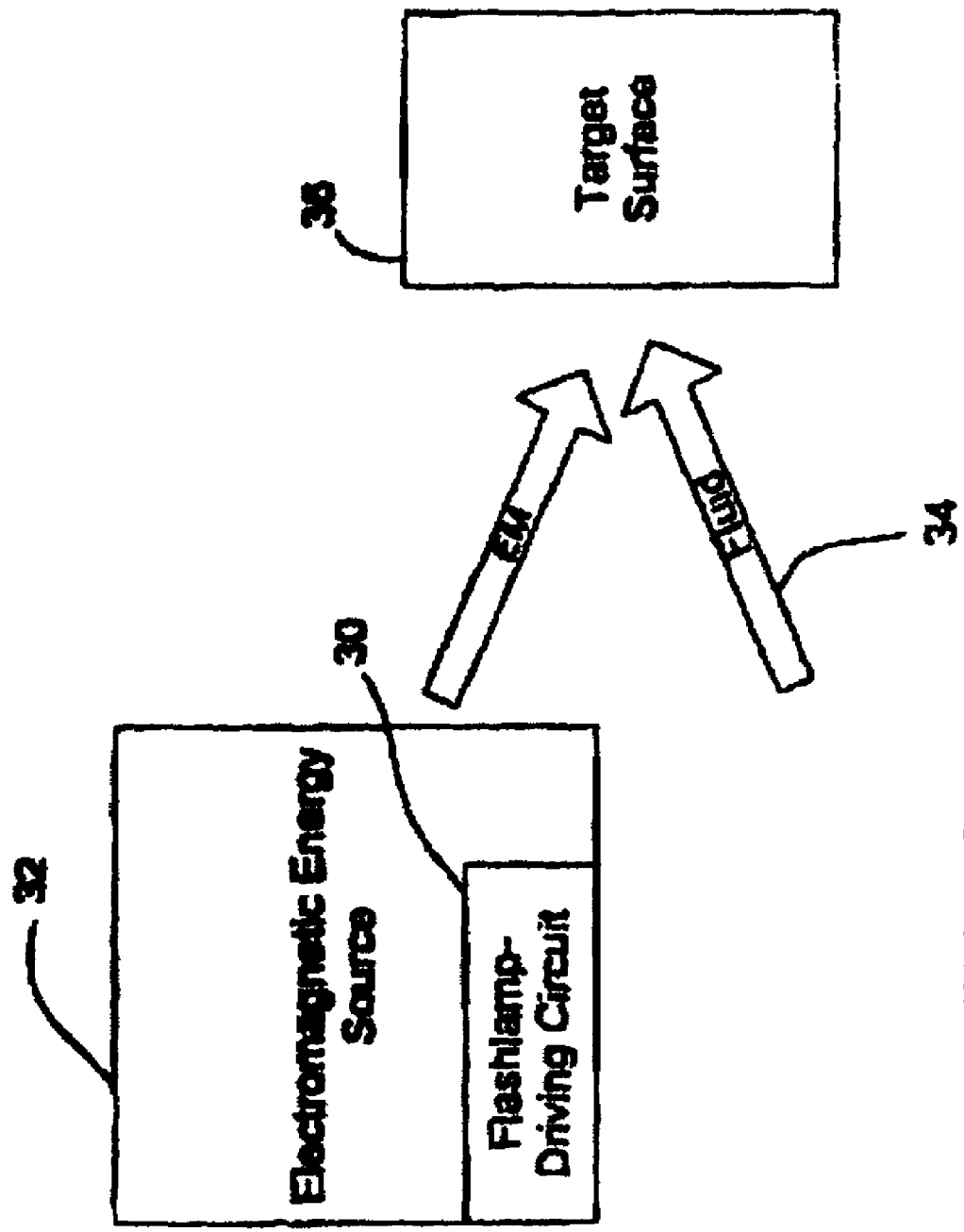
FIG. 6 is a block diagram showing a fluid output used in combination with an electromagnetic energy source having a flashlamp driving circuit in accordance with the present invention.
Figure 6A:
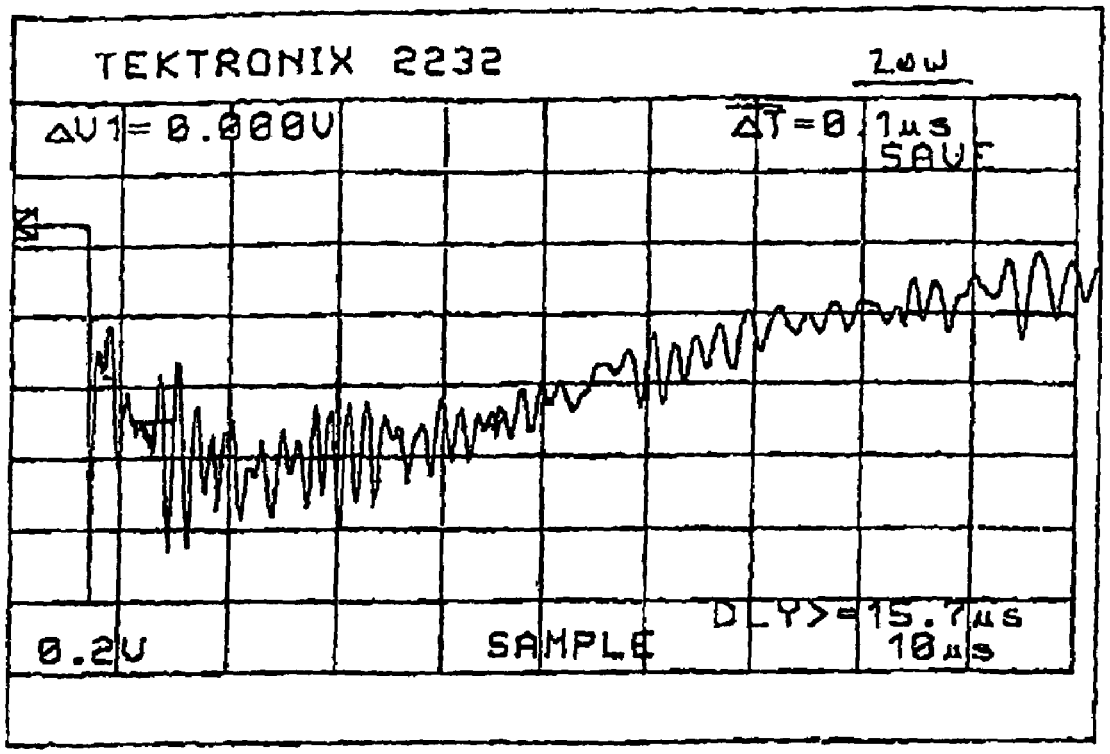
FIG. 6a is a representation corresponding to a preferred pulse shape.

The output optical energy distribution 60 of the present invention is useful for maximizing a cutting effect of an electromagnetic energy source 32, such as a laser driven by the flashlamp driving circuit 30, directed into an atomized distribution of fluid particles 34 above a target surface 36, as shown in FIG. 6. An apparatus for directing electromagnetic energy into an atomized distribution of fluid particles above a target surface is disclosed in U.S. Pat. No. 5,741,247, entitled ATOMIZED FLUID PARTICLES FOR ELECTROMAGNETICALLY INDUCED CUTTING. The high-intensity leading micropulses 64, 66, and 68 impart large amounts of energy into atomized fluid particles which preferably comprise water, to thereby expand the fluid particles and apply mechanical cutting forces to the target surface of, for example, tooth enamel, tooth dentin, tooth cementum, bone, and cartilage, skin, mucosa, gingiva, muscle, heart, liver, kidney, brain, eye or vessels. The trailing micropulses after the maximum micropulse 68 have been found to further enhance the cutting efficiency. According to the present invention, a single large leading micropulse 68 may be generated or, alternatively, two or more large leading micropulses 68 (or 64, 66, for example) may be generated.

The incoherent light from the presently preferred flashlamp 41 impinges on the outer surface of the laser rod. As the incoherent light penetrates into the laser rod, impurities within the laser rod absorb the penetrating light and subsequently emit coherent light. The impurities may comprise erbium and chromium, and the laser rod itself may comprise a crystal such as YSGG, for example. The presently preferred laser system comprises either an Er, Cr:YSGG solid state laser, which generates electromagnetic energy having a wavelength in a range of 2.70 to 2.80 microns, or an erbium, yttrium, aluminum garnet (Er:YAG) solid state laser, which generates electromagnetic energy having a wavelength of 2.94 microns. As presently preferred, the Er, Cr:YSGG solid state laser has a wavelength of approximately 2.78 microns and the Er:YAG solid state laser has a wavelength of approximately 2.94 microns According to one alternative embodiment, the laser rod may comprises a YAG crystal, and the impurities may comprise erbium impurities. A variety of other possibilities exist, a few of which are set forth in the above-mentioned book Solid-State Laser Engineering, Fourth Extensively Revised and Updated Edition, by Walter Koechner, published in 1996, the contents of which are expressly incorporated herein by reference Other possible laser systems include an erbium, yttrium, scandium, gallium garnet (Er:YSGG) solid state laser, which generates electromagnetic energy having a wavelength in a range of 2.70 to 2.80 microns; an erbium, yttrium, aluminum garnet (Er:YAG) solid state laser, which generates electromagnetic energy having a wavelength of 2.94 microns; chromium, thulium, erbium, yttrium, aluminum garnet (CTE:YAG) solid state laser, which generates electromagnetic energy having a wavelength of 2.69 microns; erbium, yttrium orthoaluminate (Er:YAL03) solid state laser, which generates electromagnetic energy having a wavelength in a range of 2.71 to 2.86 microns; holmium, yttrium, aluminum garnet (Ho:YAG) solid state laser, which generates electromagnetic energy having a wavelength of 2.10 microns; quadrupled neodymium, yttrium, aluminum garnet (quadrupled Nd:YAG) solid state laser, which generates electromagnetic energy having a wavelength of 266 nanometers; argon fluoride (ArF) excimer laser, which generates electromagnetic energy having a wavelength of 193 nanometers; xenon chloride (XeCl) excimer laser, which generates electromagnetic energy having a wavelength of 308 nanometers; krypton fluoride (KrF) excimer laser, which generates electromagnetic energy having a wavelength of 248 nanometers; and carbon dioxide ($CO_2$), which generates electromagnetic energy having a wavelength in a range of 9 to 11 microns.

Particles, such as electrons, associated with the impurities absorb energy from the impinging incoherent radiation and rise to higher valence states. The particles that rise to metastable levels remain at this level for periods of time until, for example, energy particles of the radiation excite stimulated transitions. The stimulation of a particle in the metastable level by an energy particle results in both of the particles decaying to a ground state and an emission of twin coherent photons (particles of energy). The twin coherent photons can resonate through the laser rod between mirrors at opposing ends of the laser rod, and can stimulate other particles on the metastable level, to thereby generate subsequent twin coherent photon emissions. This process is referred to as light amplification by stimulated emission. With this process, a twin pair of coherent photons will contact two particles on the metastable level, to thereby yield four coherent photons. Subsequently, the four coherent photons will collide with other particles on the metastable level to thereby yield eight coherent photons.

The amplification effect will continue until a majority of particles, which were raised to the metastable level by the stimulating incoherent light from the flashlamp 41, have decayed back to the ground state. The decay of a majority of particles from the metastable state to the ground state results in the generation of a large number of photons, corresponding to an upwardly rising micropulse (64, for example, FIG. 5). As the particles on the ground level are again stimulated back up to the metastable state, the number of photons being emitted decreases, corresponding to a downward slope in the micropulse 64, for example The micropulse continues to decline, corresponding to a decrease in the emission of coherent photons by the laser system. The number of particles stimulated to the metastable level increases to an amount where the stimulated emissions occur at a level sufficient to increase the number of coherent photons generated. As the generation of coherent photons increases, and particles on the metastable level decay, the number of coherent photons increases, corresponding to an upwardly rising micropulse.

Figure 5:
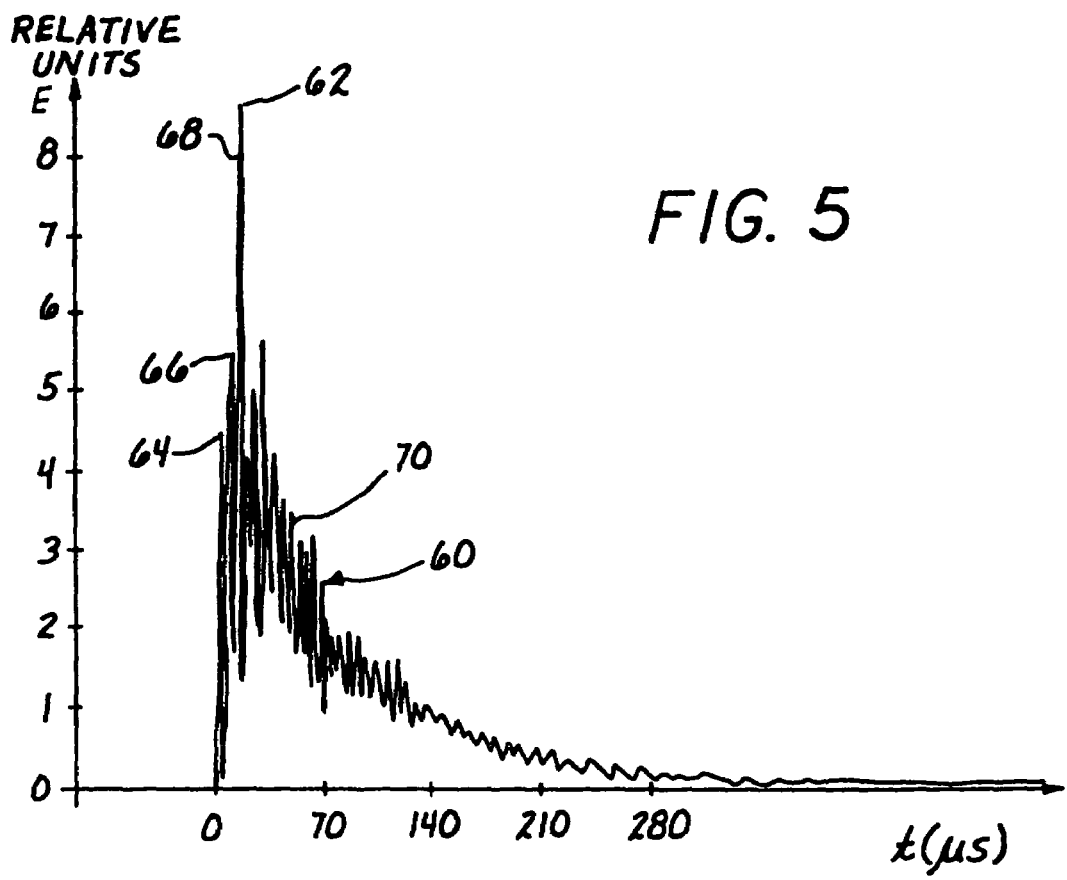
FIG. 5 is a plot of output optical energy versus time for a laser system in accordance with the present invention.

The output optical energy distribution over time of the laser system is illustrated in FIG. 5 at 60. The output optical energy distribution of the present invention preferrably has a pulse width that is greater than about 0.25 microseconds and, more preferrably, in a range of 125 to 300 mircoseconds. In the illustrated embodiment, the pulse width is about 200 microseconds. The output optical energy distribution 60 comprises a maximum value 62, a number of leading micropulses 64, 66, 68, and a portion of generally declining optical energy 70.

According to the present invention, the output optical energy distribution 60 comprises a large magnitude. This large magnitude corresponds to one or more sharply-rising micropulses at the leading edge of the pulse. As illustrated in FIG. 5, the micropulse 68 comprises a maximum value 62 which is at or near the very beginning of the pulse. Additionally, the full-width half-max value of the output optical energy distribution in FIG. 5 is approximately 70 microseconds, compared to full-width half-max values of the prior art typically ranging from 250 to 300 microseconds. Applicant's invention contemplates pulses comprising full-width half-max values greater than 0.025 microseconds and, preferably, ranging from 10 to 150 microseconds, but other ranges may also be possible. Additionally, Applicant's invention contemplates a pulse width of between 0.25 and 300 microseconds, for example, compared to typical prior-art pulse widths which are greater than 300 microseconds. Further, a frequency of 20Hz is presently preferred alternatively, a frequency of 30 Hz may be used. Applicants' invention generally contemplates frequencies between 1 and 100 Hz, compared to prior art frequencies typically ranging from 1 to 15 Hz.

As mentioned above, the full-width half-max range is defined from a beginning time, where the amplitude first rises above one-half the peak amplitude, to an ending time, where the amplitude falls below one-half the peak amplitude a final time during the pulse width. The full-width half-max value is defined as the difference between the beginning time and the ending time.

The location of the full-width half-max range along the time axis, relative to the pulse width, is closer to the beginning of the pulse than the end of the pulse. The location of the full-width half-max range is preferably within the first half of the pulse and, more preferably, is within about the first third of the pulse along the time axis. Other locations of the full-width half-max range are also possible in accordance with the present invention. The beginning time preferably occurs within the first 10 to 15 microseconds and, more preferably, occurs within the first 12.5 microseconds from the leading edge of the pulse. The beginning time, however, may occur either earlier or later within the pulse. The beginning time is preferably achieved within the first tenth of the pulse width.

Another distinguishing feature of the output optical energy distribution 70 is that the micropulses 64, 66, 68, for example, comprise approximately one-third of the maximum amplitude 62. More preferably, the leading micropulses 64, 66, 68 comprise an amplitude of approximately one-half of the maximum amplitude 62. In contrast, the leading micropulses of the prior art, as shown in FIG. 2, are relatively small in amplitude.

The slope of the output optical energy distribution 60 is greater than or equal to 5 and, more preferably, is greater than about 10. In the illustrated embodiment, the slope is about 50. In contrast, the slope of the output optical energy distribution 20 of the prior art is about 4.

The output optical energy distribution 60 of the present invention is useful for maximizing a cutting effect of an electromagnetic energy source, such as a laser, directed into an atomized distribution of fluid particles above a target surface. An apparatus for directing electromagnetic energy into an atomized distribution of fluid particles above a target surface is disclosed in co-pending U.S. application Ser. No. 08/522,503, filed Aug. 31, 1995 and entitled USER PROGRAMMABLE COMBINATION OF ATOMIZED PARTICLES FOR ELECTROMAGNETICALLY INDUCED CUTTING. The high-intensity leading micropulses 64, 66, and 68 impart large amounts of energy into atomized fluid particles which preferably comprise water, to thereby expand the fluid particles and apply mechanical cutting forces to the target surface. The trailing micropulses after the maximum micropulse 68 have been found to further enhance the cutting efficiency. According to the present invention, a single large leading micropulse 68 may be generated or, alternatively, two or more large leading micropulses 68 (or 64, 66, for example) may be generated.

The flashlamp current generating circuit 30 of the present invention generates a relatively narrow pulse, which is on the order of 0.25 to 300 microseconds, for example. Additionally, the full-width half-max value of the optical output energy distribution 60 of the present invention preferably occurs within the first 70 microseconds, for example, compared to full-width half-max values of the prior art occurring within the first 250 to 300 microseconds. The relatively quick frequency, and the relatively large initial distribution of optical energy in the leading portion of each pulse of the present invention, results in efficient mechanical cutting. If a number of pulses of the output optical energy distribution 60 were plotted, and the average power determined, this average power would be relatively low, compared to the amount of energy delivered to the laser system via the high-voltage power supply 33. In other words, the efficiency of the laser system of the present invention may be less than typical prior art systems. Since the output optical energy distributions of the present invention are uniquely adapted for imparting electromagnetic energy into atomized fluid particles over a target surface, however, the actual cutting of the present invention is optimized. The cutting effect obtained by the output optical energy distributions of the present invention is both clean and powerful and, additionally, provides a consistent cut. The terms "cut" and "cutting" are broadly defined herein as imparting disruptive mechanical forces onto the target surface.

In accordance with one aspect of the present invention, an apparatus is provided, comprising a current generating circuit; an excitation source operatively coupled to the current generating circuit, the excitation source comprising at least one laser diode and being configured to operate at a frequency within a range from about 1 to about 100 Hz; and a gain medium coupled to be side pumped by the excitation source and to output electromagnetic energy.

Accordance to another aspect of the present invention, a method is provided, comprising providing a current generating circuit; providing an excitation source operatively coupled to the current generating circuit, the excitation source comprising at least one laser diode and being configured to operate at a frequency within a range from about 1 to about 100 Hz; and activating the excitation source to side pump a gain medium, whereby the gain medium outputs electromagnetic energy.

In accordance with another aspect of the present invention, an apparatus for cutting or ablating hard tissue comprises an optical cavity; a gain medium disposed within the optical cavity; and a diode light pump disposed within the optical cavity and optically aligned to light pump the gain medium to generate laser light, wherein the generated laser light has a wavelength and power density suitable for cutting and ablating hard tissue.

A method of cutting or ablating hard tissue according to a further aspect of the present invention comprises the steps of providing a gain medium, a diode light pump, and an optical cavity; placing the gain medium and the diode light pump within the optical cavity so that the diode light pump is optically aligned to light pump the gain medium; activating the diode light pump to light pump the gain medium and generate laser light; and directing the laser light onto the hard tissue to cut or ablate the hard tissue.

According to another aspect of the invention, a method of cutting or ablating hard tissue is disclosed, comprising the steps of providing a gain medium, a diode array, and an optical cavity; placing the gain medium and the diode array within the optical cavity so that the diode array is optically aligned to side pump the gain medium; activating the diode array to light pump the gain medium and generate laser light; and directing the laser light onto the hard tissue to cut or ablate the hard tissue.

An apparatus for imparting disruptive forces onto a target surface, according to another aspect, comprises: a fluid output configured to place fluid into a volume in close proximity to the target surface; and an excitation source configured to direct electromagnetic energy into the volume in close proximity to the target surface, wherein the excitation source outputs the electromagnetic energy in a form of at least one output pulse having a plurality of high-intensity leading micropulses that impart relatively large amounts of energy into at least part of the fluid in the volume, the relatively large amounts of energy imparted into the fluid being sufficient to cause the fluid to expand wherein disruptive cutting or ablating forces onto to the target surface, the excitation source being configured to operate at a frequency within a range from about 1 to about 100 Hz.

A method of cutting or ablating hard tissue is also provided in accordance with an aspect of the present invention, comprising the following steps: placing fluid into a volume in close proximity to the hard tissue; and activating an excitation source comprising at least one laser diode to light pump a gain medium and generate laser light in a form of at least one output pulse having a plurality of high-intensity leading micropulses, the laser light having a wavelength which is highly absorbed by the fluid, the excitation source being configured to operate at a frequency within a range from about 1 to about 100 Hz. The method can comprise directing the at least one output pulse into the volume to impart relatively large amounts of energy into at least part of the fluid in the volume, the relatively large amounts of energy causing the fluid to expand wherein disruptive cutting or ablating forces are imparted to the target surface.

In any of the above aspects, the gain medium may comprise a laser rod, such as an Erbium-based laser rod. More particularly, the gain medium may comprise an Erbium-based crystalline laser rod for generating laser light in a range between 1.73 and 2.94 microns. The laser light can have a wavelength in a range from about 2.69 um to about 2.95 um.

The laser light can be generated in the TEMoo mode to overcome-thermal effects. The generated laser light can have a wavelength, pulse, and power density suitable for cutting and ablating tooth tissue tissue or bone. Thus, in accordance with a method of the present invention, the hard tissue can comprise, for example, tooth or bone tissue. Temporal pulse control can be used to attain a uniform temporal pulse pattern. In another embodiment, gain switching or Q-switching can be used to attain the uniform temporal pulse pattern. The diode light pump or the at least one diode can comprise a diode array, and the diode array can be optically aligned to side pump the gain medium. The diode light pump can be placed within the optical cavity so that the diode array is optically aligned to side pump the gain medium. The generated laser light can have a wavelength that is highly absorbed by the fluid. The fluid can comprise water.

The methods and apparatuses of this application are intended for use, to the extent the technology is compatible, with existing technologies including the apparatuses and methods disclosed in any of the following patents and patent applications: U.S. Pat. Nos. 7,108,693; 7,068,912; 6,942,658; 6,829,427; 6,821,272; 6,744,790; 6,669,685; 6,616,451; 6,616,447; 6,610,053; 6,567,582; 6,561,803; 6,544,256; 6,533,775; 6,389,193; 6,350,123; 6,288,499; 6,254,597; 6,231,567; 6,086,367; 5,968,037; 5,785,521; and 5,741,247; and U.S. application Ser. Nos. 10/858,557, filed Jun. 1, 2004 and 5 10/178,080, filed Jun. 21, 2002 the entire contents of all which are incorporated herein by reference.

The diode side pumped Erbium crystalline laser of the present invention may emit at wavelengths between 1.73 and 2.94 μm. The pumping may be accomplished by InGaAs laser diodes configured as bars or arrays emitting at 968 nm, and can be delivered in either a CW (continuous wave) or a QCW (quasi-continuous wave) mode of operation, at power levels that may begin at 40 W. With an optimized output coupling, the light-to-light efficiency can be at least 10% and can reach a magnitude up to 35%. One of the embodiments of this invention is that these efficiency magnitudes are higher than those which may have been previously attained, owing to the inventive design which seeks to maximize the pump-to-laser mode overlap and to optimize outcoupling, specifically tailoring the outcoupling to the pulse format or CW operation of the laser.

The oscillator of the present invention is a plano-plano resonator comprising a high reflectivity mirror and an outcoupling, partially transmitting mirror. For certain applications intracavity elements, such as an electro-optic or acousto-optic cell for Q-switching, or an etalon for wavelength tuning can be introduced. The laser can emit energy in, for example, one of the following modes of operation: CW, gain switched obtained by quasi-CW operation of the pump laser diode, and Q-switched by an acousto-optical (AO) device or Q-switched by an electro-optical (EO) device. Thermal management and temperature control are provided by either air and/or water cooling, with the possibility of using thermo-electric cooling.

In the category of the disclosed diode side pumped lasers included are the following crystals: Er:LiYF$_4$ (Er:YLF) emitting at 1.73 μm on the Er$^{3+4}$I$_{13/2}$ ⇒ $^4$I$_{15/2}$ transition; Er:LiYF$_4$ emitting at 2.80 μm on the Er$^{3+4}$I$_{11/2}$ ⇒ $^4$I$_{13/2}$ transition; Er:Y$_x$Sc$_2$GasO$_{12}$ (Er:YSGG) emitting at 2.79 μm on the Er$^{3+4}$I$_{11/2}$ ⇒ $^4$I$_{13/2}$ transition; Er:Gd$_3$Sc$_2$GasO$_{12}$ (Er:GSGG) emitting at 2.8 μm on the Er$^{3+4}$I$_{11/2}$ ⇒ $^4$I$_{13/2}$ transition; Er:Gd$_3$GasO$_{12}$ (Er:GGG) emitting at 2.82 μm on the Er$^{3+4}$I$_{11/2}$ ⇒ $^4$I$_{13/2}$ transition; Er,Tm:Y$_3$Al$_5$O$_{12}$ (TE:YAG) emitting at 2.69 μm on the Er$^{3+4}$I$_{11/2}$ ⇒ $^4$I$_{13/2}$ transition; Er:KYF$_4$ emitting at 2.81 μm on the Er$^{3+4}$I$_{11/2}$ ⇒ $^4$I$_{13/2}$ transition; Ho,Yb:KYF$_4$ emitting at 2.84 μm on the Ho$^{3+5}$I$_6$ ⇒ $^5$I$_7$ transition; Er:Y$_3$Al$_5$O$_{12}$ (Er:YAG) emitting at 2.94 μm on the Er$^{3+4}$I$_{11/2}$ ⇒ $^4$I$_{13/2}$ transition; Er:Y$_3$AlO$_3$ (Er:YALO) emitting at 2.71 μm on the Er$^{3+4}$I$_{11/2}$ ⇒ $^4$I$_{13/2}$ transition; Er:KGd (WO$_4$)$_s$ (Er:KGW) emitting at 2.8 μm on the Er$^{3+4}$I$_{11/2}$⇒$^4$I$_{13/2}$ transition; Er:KY(WO$_4$)$_s$ (Er:KYW); Er:Al$_3$O$_3$ emitting on the Er$^{3+4}$I$_{11/2}$⇒$^4$I$_{13/2}$ transition; Er:Lu$_2$O$_3$ emitting at emitting at 2.71 μm on the Er$^{3+4}$I$_{11/2}$⇒$^4$I$_{13/2}$ transition; Er:CaF$_2$ emitting at 2.75-2.85 μm on the Er$^{3+4}$I$_{11/2}$⇒$^4$I$_{13/2}$ transition; Cr,Tm,Er:Y$_3$Al$_5$O$_{12}$ (CTE:YAG) emitting at 2.71 μm on the Er$^{3+4}$I$_{11/2}$⇒$^4$I$_{13/2}$ transition; Er:BaLu$_2$F$_8$ emitting at 2.8 μm on the Er$^{3+4}$I$_{11/2}$⇒$^4$I$_{13/2}$ transition; Er:BaY$_2$F$_8$ (Er:BYF) emitting at 2.7 μm on the Er$^{3+4}$I$_{11/2}$⇒$^4$I$_{13/2}$ transition; and Cr:ZnSe emitting at 2-3 μm.

Due to their efficient interaction with biological tissue and water, these lasers are useful as surgical instruments, in the areas of, for example, dental surgery, orthopedic surgery, tissue ablation, bone cutting and soft tissue surfacing. Particular applications may include use of the laser for expansion of atomized water or fluid particles above a target surface for mechanical cutting or ablation, such as disclosed in U.S. Pat. No. 5,741,247, entitled Atomized Fluid Particles for Electromagnetically Induced Cutting, and U.S. Pat. No. 5,785,521, entitled "Fluid Conditioning System," the contents of which are expressly incorporated herein by reference.

Another embodiment of the side diode pumped erbium lasers and Ho,Yb:KYF4 laser is that when operated in pulses, the pulsed format is highly repetitive in time and intensity. This performance can facilitate precise and predictable cutting, and can improve cutting efficiency. In dental and medical applications, this feature is consistent with less heat or thermal denaturation of the tissue, which can provide for quicker healing.

Figure 1A:
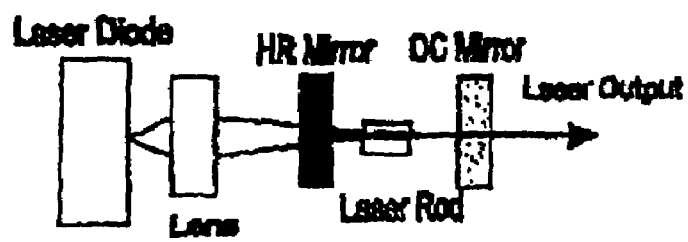
FIG. 1a is a schematic illustration of an end-pumped diode laser in accordance with the prior art.
Figure 2A:
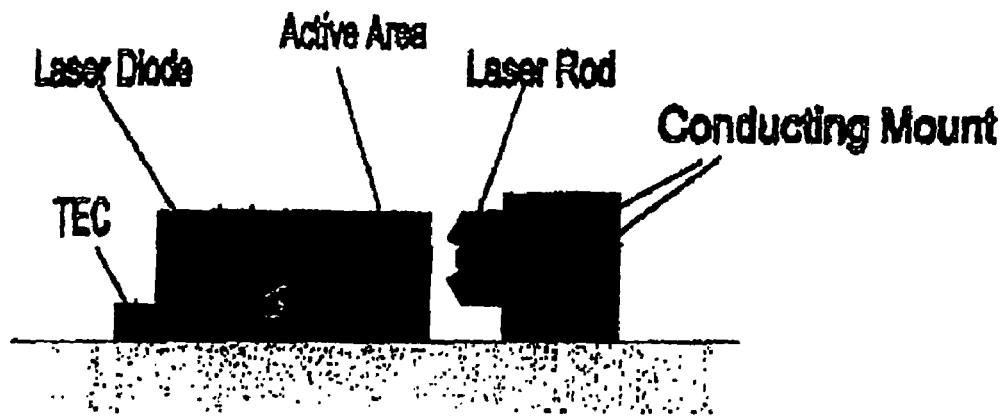
FIG. 2a is a schematic top view of a laser head according to the present invention.
Figure 2B:
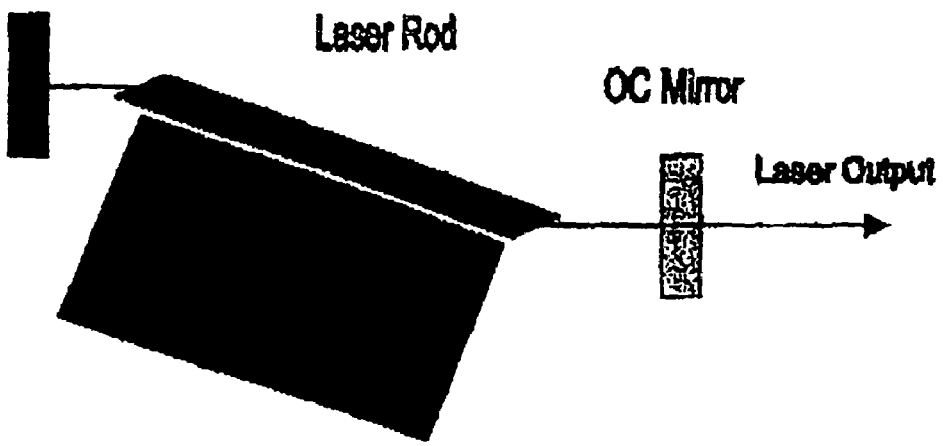
FIG. 2b is a schematic side view of a laser head according to the present invention.

The present invention is configured as shown in FIGS. 1a, 2a and 2b. It applies the side-pumped configuration to: 1) pumping of erbium and Ho,Yb:KYF4 crystals to extract laser emission in the 1.73 and 2.94 μm range, 2) dental and medical cutting and resurfacing by mainly the 2.69 to 2.95 μm range, 3) optimization of the dental and medical process by efficient delivery of the laser to the target and minimal thermal process. Configuration of the crystal itself can be rectangular or round. A rectangular shape may be preferred in one embodiment, although a cylindrical shape may function well in modified embodiments. The pumping wavelength should be chosen to be efficiently transferred into the crystal, wherein for example the radiation wavelength of the diode pumping source matches a peak absorption of the active media or crystal. In one embodiment a lens may be used to couple the pump source to the laser rod. Cooling sources and/or lenses may be positioned between the pump source and the laser rod. Regarding FIGS. 2a and 2b, FIG. 2a is a schematic top view of a laser head according to the present invention wherein "TEC" denotes thermo electric cooler, and FIG. 2b is a schematic side view of a laser head according to the present invention wherein opposing ends of the laser rod are cut to the Brewster angle to provide polarization.

Figure 3A:
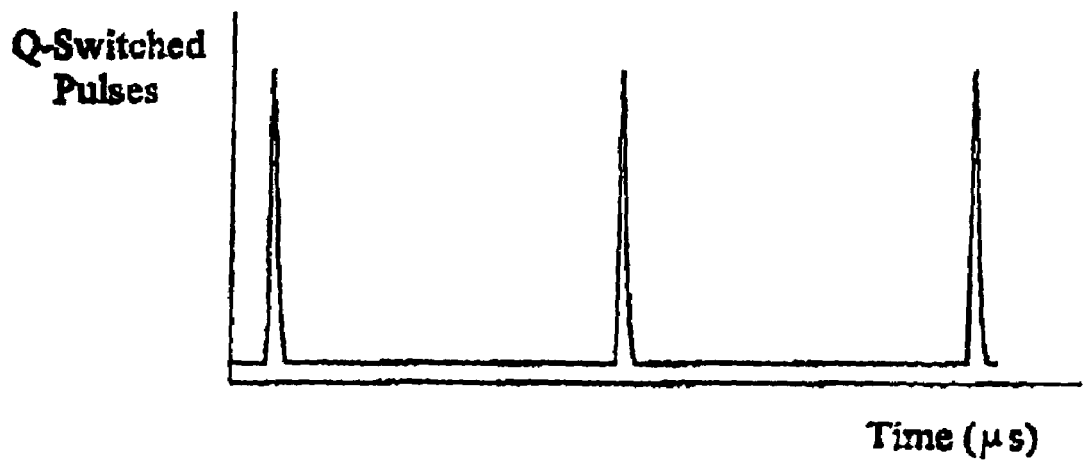
FIG. 3a is a regulated laser pulse format according to the present invention.

Regarding the present invention's application of the side-pumped configuration to optimize dental and medical processes by efficient delivery of the laser to the target and minimal thermal process, optimization is accomplished by radiating the target with a train of well regulated pulses, as shown in FIG. 3a. What is shown is a sequence of narrow pulses, each having a sufficiently high power, for instance 20 kW, and an energy of 8 mJ. With a duty cycle of 0.02% this determines an average power of 4W. A number of methods may be employed to attain such a pulse format, among them: gain switching and Q-switching by either an electro-optical or an acousto-optical Q-switch.

Figure 4C:
FIG. 4c shows the resulting laser pulse from FIGS. 4a and 4b according to the present invention.
Figure 1B:
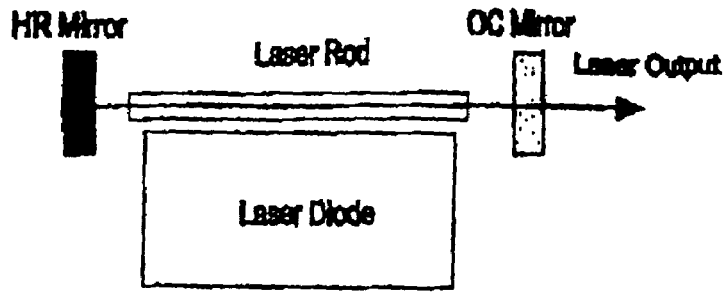
FIG. 1b is a side-pumped diode laser according to the present invention.
Figure 4A:
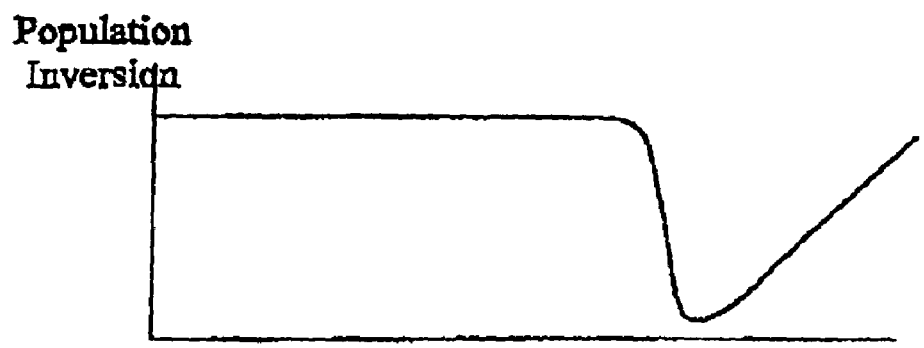
FIG. 4a shows the population inversion in a CW pumping regime according to the present invention.
Figure 4B:
FIG. 4b shows the resonator Q due to the Q-switch hold-off according to the present invention.
Figure 4:
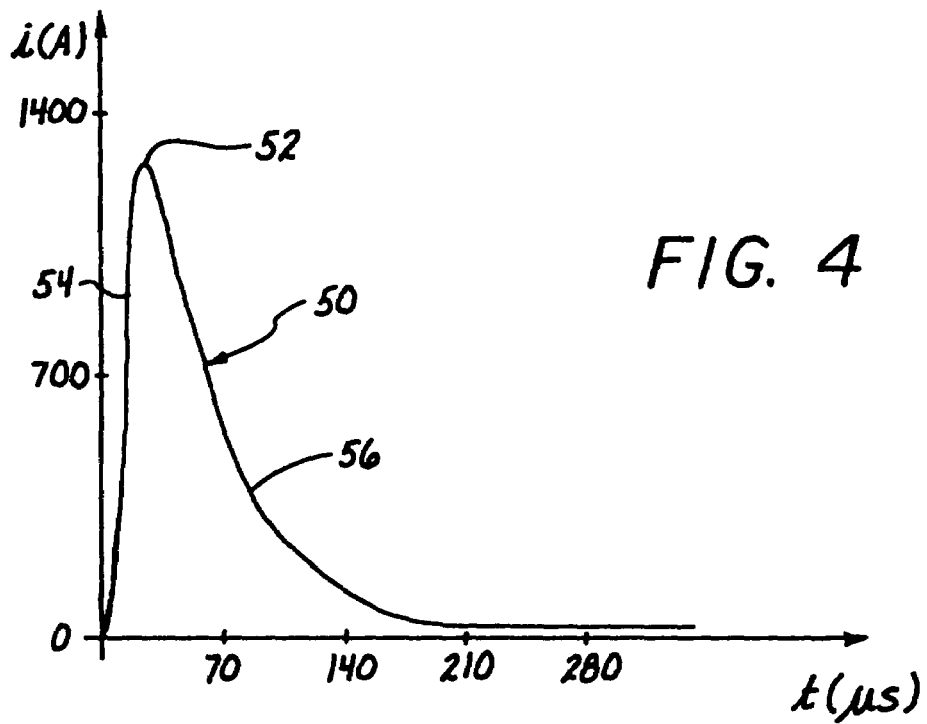
FIG. 4 is a plot of flashlamp-driving current versus time in accordance with the present invention.
Figure 5A:
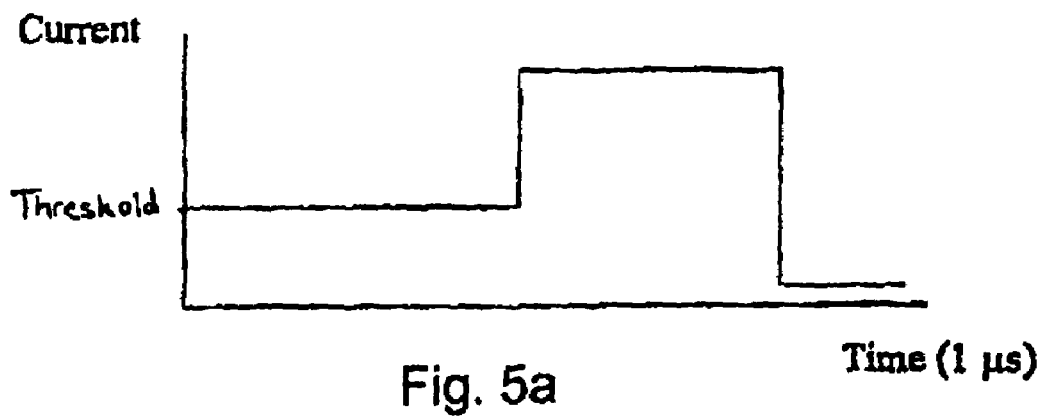
FIG. 5a shows the quasi CW current supplied to the pumping laser diode according to the present invention.
Figure 5B:
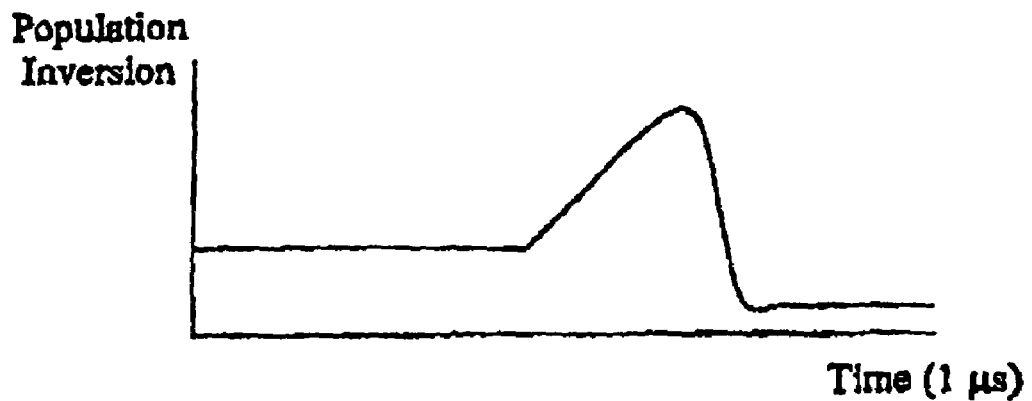
FIG. 5b shows the population inversion in the quasi CW pumping according to the present invention.
Figure 5C:
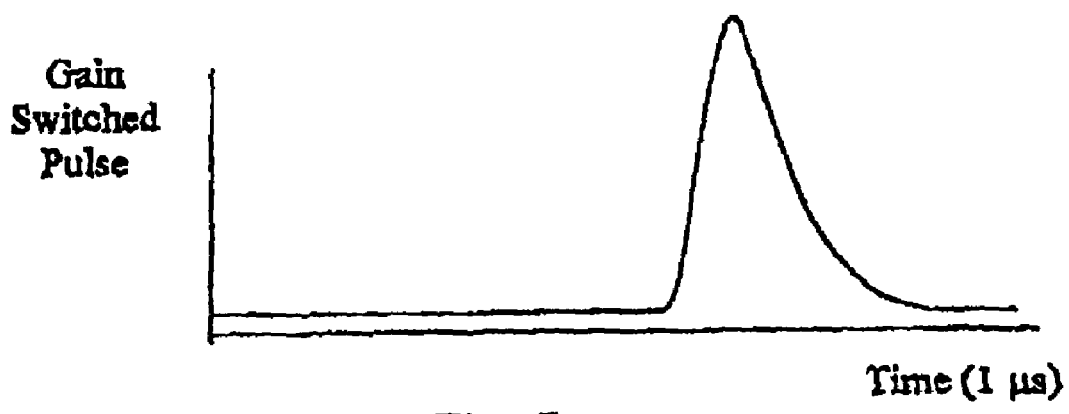
FIG. 5c shows resulting laser pulse from FIGS. 5a and 5b according to the present invention.
Figure 7:
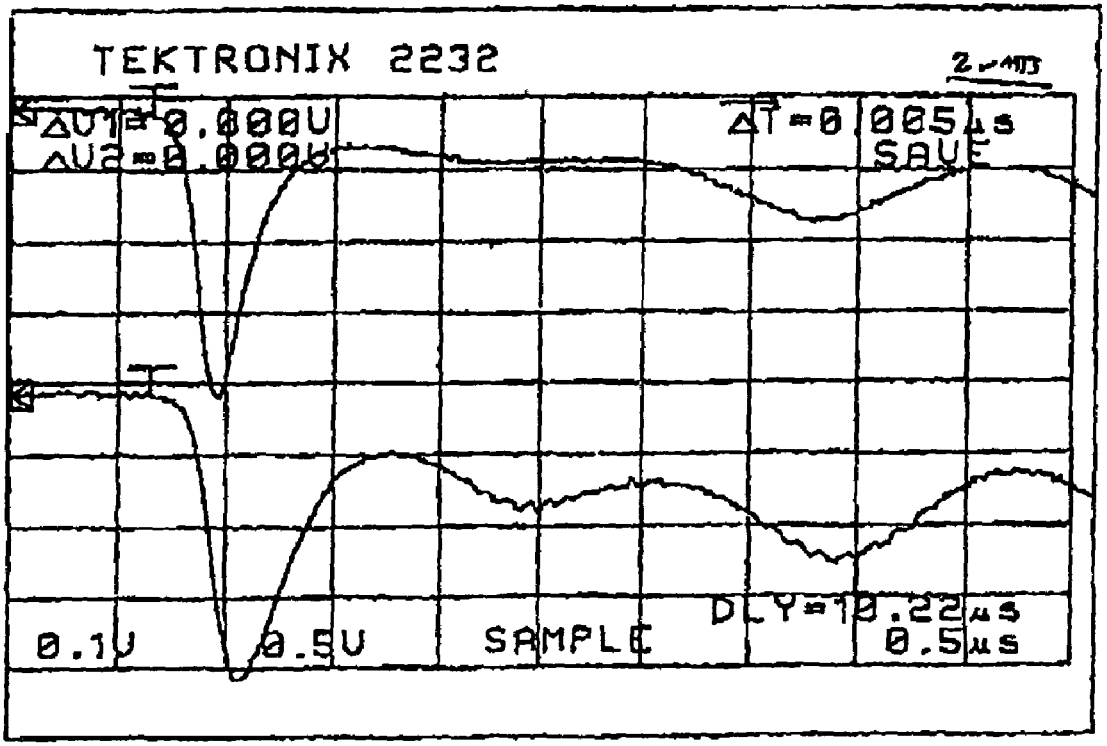

The Q-switch temporal trace is shown in FIGS. 4a-4c, wherein FIG. 4a shows the population inversion in a CW pumping regime, FIG. 4b shows the resonator Q due to the Q-switch hold-off, and FIG. 4c corresponds generally to FIG. 3a and shows the resulting laser pulse. The gain switch temporal trace is shown in FIGS. 5a-5c, wherein FIG. 5a shows the quasi-CW (QCW) current supplied to the pumping laser diode, FIG. 5b shows the population inversion in the QCW pumping regime and FIG. 5c shows the resulting laser pulse. Because in gain switching the resonator Q is never spoiled, the pulse evolves simultaneously with the buildup of the population inversion. Hence, the dynamics are similar to a free running laser, as in the pulse train shown in FIG. 6. However, as shown in FIG. 5a, the gain is dropped to below threshold once the first spike is generated, thus a gain switch pulse is formed as the first spike only, as shown in FIG. 7. Additional description is provided in the following table.

In view of the foregoing, it will be understood by those skilled in the art that the methods of the present invention can facilitate formation of laser devices, and in particular side-pumped diode laser systems. The above-described embodiments have been provided by way of example, and the present invention is not limited to these examples. Multiple variations and modification to the disclosed embodiments will occur, to the extent not mutually exclusive, to those skilled in the art upon consideration of the foregoing description. Such variations and modifications, however, fall well within the scope of the present invention as set forth in the following claims.

What is claimed is:

1. An apparatus for imparting disruptive forces onto a tissue target surface, comprising:
    a fluid output configured to place fluid into a volume in close proximity to the tissue target surface; and
    an excitation source configured to direct electromagnetic energy into the volume in close proximity to the tissue target surface, wherein the excitation source outputs the electromagnetic energy in a form of at least one output pulse having a plurality of high-intensity leading micropulses that impart relatively large amounts of energy into at least part of the fluid in the volume, the relatively large amounts of energy imparted into the fluid being sufficient to cause the fluid to expand wherein disruptive cutting or ablating forces are directed to the tissue target surface.

2. The apparatus as set forth in claim 1, further comprising an optical cavity and a gain medium disposed within the optical cavity, wherein the excitation source is disposed within the optical cavity and optically aligned to light pump the gain medium to generate electromagnetic energy including laser light, wherein the generated laser light has a wavelength, pulse, and power density suitable for cutting and ablating hard tissue and further has a wavelength that is highly absorbed by the fluid.

3. The apparatus as set forth in claim 1, wherein the fluid is water and the tissue target surface is cut or ablated.

4. The apparatus as set forth in claim 1, wherein:
    the excitation source is configured to operate at a frequency within a range from about 1 to about 100 Hz; and
    the generated laser light has a wavelength, pulse, and power density suitable for cutting and ablating tooth tissue.

5. The apparatus as set forth in claim 1, wherein temporal pulse control is used to attain a uniform temporal pulse pattern.

6. The apparatus as set forth in claim 1, wherein the gain medium comprises an Erbium-based crystalline laser rod for generating laser light in a range between 1.73 and 2.94 microns.

7. The apparatus as set forth in claim 6, wherein the laser light is generated in the TEMoo mode.

8. The apparatus as set forth in claim 6, wherein the generated laser light has a wavelength, pulse, and power density suitable for cutting and ablating tooth tissue.

9. The apparatus as set forth in claim 8, wherein the fluid is water.

10. The method as set forth in claim 9, wherein the laser light has a wavelength in a range from about 2.69 um to about 2.95 um.

11. A method of cutting or ablating hard tissue, comprising the following steps:
   placing fluid into a volume in close proximity to the hard tissue; and
   activating an excitation source to light pump a gain medium and generate laser light in a form of at least one output pulse having a plurality of high-intensity leading micropulses, the laser light having a wavelength which is highly absorbed by the fluid.

12. The method as set forth in claim 11, wherein the method further comprises directing the at least one output pulse into the volume to impart relatively large amounts of energy into at least part of the fluid in the volume, the relatively large amounts of energy causing the fluid to expand wherein disruptive cutting or ablating forces are imparted to the tissue target surface.

13. The method as set forth in claim 11, wherein:
   the gain medium comprises a laser rod;
   the fluid comprises water;
   the excitation source comprising at least one laser diode that is configured to operate at a frequency within a range from about 1 to about 100 Hz; and
   the excitation source comprises a diode array that is optically aligned to side pump the laser rod.

14. The method as set forth in claim 11, wherein the gain medium comprises an Erbium-based laser rod.

15. The method as set forth in claim 11, wherein the laser light is generated in the TEMoo mode.

16. The method as set forth in claim 11, wherein the hard tissue comprises tooth tissue.

17. The method as set forth in claim 11, wherein the hard tissue comprises bone.

18. The method as set forth in claim 11, wherein temporal pulse control is used to attain a uniform temporal pulse pattern.

19. The method as set forth in claim 11, wherein the laser light has a wavelength in a range from about 2.69 um to about 2.95 um.

* * * * *

UNITED STATES PATENT AND TRADEMARK OFFICE
CERTIFICATE OF CORRECTION

PATENT NO. : 7,415,050 B2  
APPLICATION NO. : 11/606660  
DATED : August 19, 2008  
INVENTOR(S) : Ioana M. Rizoiu et al.

It is certified that error appears in the above-identified patent and that said Letters Patent is hereby corrected as shown below:

Title Page, item (63) should read

-- This application is a continuation-in-part of co-pending U.S. Application No. 11/523,492, filed September 18, 2006 and entitled ELECTROMAGNETIC ENERGY DISTRIBUTIONS FOR ELECTROMAGNETICALLY INDUCED MECHANICAL CUTTING (Att. Docket BI9066CON4) which is commonly assigned and the contents of which are expressly incorporated herein by reference. U.S. Application No. 11/523,492 is a continuation of U.S. Application No. 10/993,498, filed November 18, 2004 (now U.S. Patent No. 7,108,693; Att. Docket BI9066CON3), which is a continuation of U.S. Application No. 10/164,451, filed June 6, 2002 (now U.S. Patent No. 6,821,272; Att. Docket BI9066CON2), which is a continuation of U.S. Application No. 09/883,607, filed June 18, 2001 (now abandoned; Att. Docket BI9066CON), which is a continuation of U.S. Application No. 08/903,187, filed June 12, 1997 (now U.S. Patent No. 6,288,499; Att. Docket BI9066P), all of which are commonly assigned. --.

Signed and Sealed this

Fourteenth Day of December, 2010

David J. Kappos  
*Director of the United States Patent and Trademark Office*